United States Patent [19]

Charbonneau et al.

[11] Patent Number: 4,606,956
[45] Date of Patent: Aug. 19, 1986

[54] ON PAGE FRAGRANCE SAMPLING DEVICE

[75] Inventors: Jack W. Charbonneau, Somerset; Keith E. Relyea, St. Joseph, both of Wis.

[73] Assignee: Minnesota Mining and Manufacturing Company, St. Paul, Minn.

[21] Appl. No.: 742,144

[22] Filed: Jun. 7, 1985

Related U.S. Application Data

[63] Continuation of Ser. No. 684,597, Dec. 21, 1984, abandoned.

[51] Int. Cl.⁴ ................................................ G09F 3/00
[52] U.S. Cl. ........................................ 428/40; 40/2 R; 428/313.5; 428/905
[58] Field of Search ............... 428/40, 313.5, 905; 40/2 R

[56] References Cited

U.S. PATENT DOCUMENTS

| | | | |
|---|---|---|---|
| 3,016,308 | 1/1962 | MacAulay | 106/22 X |
| 3,503,783 | 3/1970 | Evans | 427/150 X |
| 3,516,846 | 6/1970 | Matson | 428/321.5 X |
| 3,516,941 | 6/1970 | Matson | 430/109 X |
| 3,623,659 | 11/1971 | Materson et al. | 428/905 X |
| 3,936,567 | 2/1976 | Vesely | 428/40 X |
| 4,058,434 | 11/1977 | Vincent et al. | 428/313.5 X |
| 4,087,376 | 5/1978 | Foris et al. | 427/151 X |
| 4,186,743 | 2/1980 | Steiger | 428/905 X |
| 4,201,404 | 5/1980 | Charbonneau et al. | 427/151 X |
| 4,397,142 | 8/1983 | Bingham | 40/2 R X |
| 4,487,801 | 12/1984 | Turnbull et al. | 428/313.5 |
| 4,514,457 | 4/1985 | Sasaki | 428/40 X |
| 4,528,226 | 7/1985 | Sweeny | 428/402.2 X |

FOREIGN PATENT DOCUMENTS

| | | |
|---|---|---|
| 1156725 | 7/1966 | United Kingdom . |
| 2006709 | 5/1979 | United Kingdom . |
| 2041319 | 9/1980 | United Kingdom . |
| 2048206 | 12/1980 | United Kingdom . |
| 2062570 | 5/1981 | United Kingdom . |

Primary Examiner—Henry F. Epstein
Attorney, Agent, or Firm—Donald M. Sell; James A. Smith; Mark A. Litman

[57] ABSTRACT

Microencapsulated materials are released by rupturing of an adhesive layer on a substrate containing the capsules. At least two sheets are secured by the adhesive layer containing the microcapsules. At least one of said two sheets has an adhesive on the outer face of said at least one sheet.

20 Claims, 1 Drawing Figure

U.S. Patent  Aug. 19, 1986  4,606,956
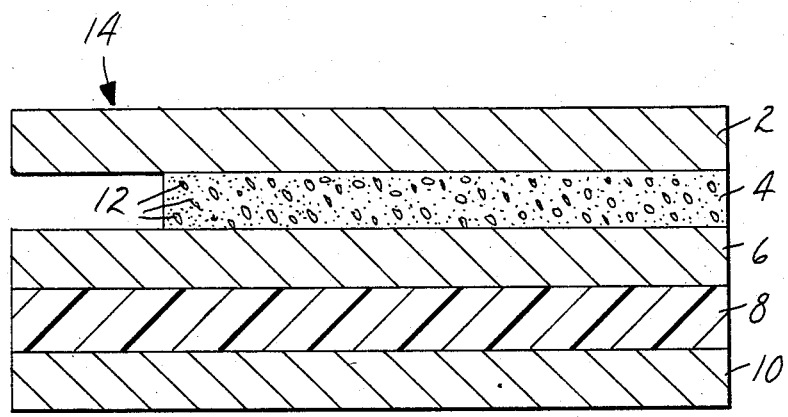

ON PAGE FRAGRANCE SAMPLING DEVICE

This is a continuation application Ser. No. 684,597 filed Dec. 21, 1984, now abandoned.

FIELD OF THE INVENTION

This invention relates to microencapsulated materials, articles containing microencapsulated materials and the method of preparing such articles. In particular, the present invention relates to labels of microencapsulated materials adhesively secured between two temporarily adhered surfaces such that upon adhesion of the label and separation of said two surfaces, the capsules rupture, releasing material contained therein.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are ruptureable by the application of heat, pressure and/or radiation because of a metal coating on the surface of the capsule. These ruptureable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; and British Patent Specification Nos. 1,156,725; 2,041,319 and 2,048,206. A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

U.S. Pat. No. 4,186,743 discloses a perfuming self-adhering sanitary napkin having a pressure-sensitive adhesive layer bonded to a strippable cover sheet having a binder layer with microcapsules on the surface thereof in contact with the pressure-sensitive adhesive layer. Upon stripping of the cover sheet, capsules are broken, the pressure sensitive adhesive is exposed and the napkin may adhere to undergarments to keep them properly positioned.

U.S. Pat. No. 4,487,801 discloses a fragrance releasing pull-apart sheet comprising a non-pressure-sensitive binder layer containing microcapsules adhered between two sheets. Upon separation of the sheets, the adhesive and capsules rupture, releasing the material within the capsules.

SUMMARY OF THE INVENTION

The present invention relates to a new article containing ruptureable microcapsules. The novel article comprises two sheets or opposed faces of a folded single sheet which are temporarily bonded by means of an adhesive with ruptureable microcapsules dispersed therein and on the exterior surface of one of said sheets is a pressure-sensitive adhesive layer. The microcapsules are ruptured by pulling apart the sheets after they are first adhered to another surface which causes the capsules to rupture and release the ingredients contained therein. By selecting the relative physical properties of the sheet, adhesive, capsules and the binding forces amongst them, a high rate of capsule rupturing can be obtained consistently.

SUMMARY OF THE DRAWING

The FIGURE shows a side view of the appliable label of the present invention.

DETAILED DESCRIPTION OF THE DRAWING

The FIGURE shows the label 14 of the present invention of a top sheet 2 secured to bottom sheet 6 by an adhesive layer 4 having rupturable microcapsules 12 therein. The surface of the bottom sheet 6 which is away from the top sheet 2 has a pressure sensitive adhesive layer 8 thereon. The pressure-sensitive adhesive layer 8 is usually protected before use by a strippable cover sheet 10.

DETAILED DESCRIPTION OF THE INVENTION

Pull-apart inserts such as those disclosed in U.S. Pat. No. 4,487,801 are usually saddle-stitched, perfect bound or center-stapled (by staples or glue) into magazines and cost as much as a full page. Even with art work (e.g., printing) on the pull apart sheets, after opening the sheets, tend to be unattractive and do not usually compare with the size and thickness of other pages in the magazines. Certain manufacturers of these inserts lack sufficient expertise to prevent the sheets from opening during transit and the magazines tend to be overwhelmed with a multiplicity of scents, thereby reducing the effectiveness of individual inserts.

The present invention relates to an article comprising at least two sheets or opposed faces of a folded single sheet temporarily secured by means of a adhesive layer having microcapsules dispersed therein, at least one exterior surface of a sheet having a pressure-sensitive adhesive thereon. The sheet materials of the present invention comprise any sheet or film forming material, particularly paper and most preferably coated paper. Generally flexible sheets of paper are preferred although polymeric films may be used. Coated paper is a conventional and standard item in commerce. It is generally a fibrous sheet having a pigment-bearing resinous coating on one or both surfaces. Usually the pigment provides a white, bone or ivory coloration to the sheet. Most generally pigments producing a white coloration are used. The binder used in the resinous coating is generally colorless and/or transparent. The binder is generally a synthetic or natural organic polymeric material. Typical pigments for producing white coated paper are fine white pigment such as clay, calcium carbonate, titania, silica, zinc oxide, etc. Typical binders include latices (e.g., styrene-butadiene, butadiene-acrylonitrile, etc.), film-forming polymers (e.g., polymethylmethacrylate), and natural resins (e.g., casein, ammonium caseinate, starch, etc.). The coatings usually comprise between 65-90% by weight of pigment, preferably 70-80% by weight of pigment, and 10-35% by weight of binder, preferably 20-30% by weight of binder. Papers having both sides coated are preferred in the advertising trade.

The adhesive material for the capsules must form a bond to the coated surfaces of the sheets which is stronger than the cohesive strength of the adhesive with the capsules dispersed therein. Although it is generally desirable to have an adhesive, the absolute cohesive strength of which is less than its adhesive strength to the coated surface of the coated paper cover sheets, this is not essential. When capsules are included within the adhesive composition, the effective cohesive strength of the adhesive tends to be reduced. Adhesives, which by themselves would cause the sheets to be damaged during separation, can be used in combination with capsules in the practice of the present invention because of lowered effective cohesive strength. The capsules in the present invention may comprise any ruptureable capsule containing an active ingredient therein. The tensile rupture strength of the capsules must be such that the cohesive failure of the adhesive results in capsule breakage. It has also been found that the size of the capsules plays a role in the usefulness of capsules within ruptureable sheets according to the practice of the present invention. Generally the capsules should have an average diameter between 6 and 50 microns and preferably between 12 and 30 microns when the capsule payload is between 80 and 90% by weight of the total capsule weight. It is highly preferred that the capsules have an average diameter between 14 and 26 microns and it is most preferred that the capsules have a diameter between 15 and 25 microns. These dimensions play a surprisingly important role in the ability to control the percentage of rupture of capsules in the practice of the present invention. With lower payloads (e.g., 70-80%), the capsules should be larger to provide the necessary rupture strength. The broadest range of capsule size under any conditions would be about 4 to 80 microns, with 8 micron capsules used with a 90-95% by weight payload. Eight to thirty micron capsules are generally preferred.

Any pressure-sensitive adhesive may be used in the exterior surface of one of said sheets. Typically, acrylate and polyurethane pressure-sensitive adhesives are used to bond the article to another surface.

A basic relationship exists amongst the factors of peel force adhesive coating weight and the median capsule diameter. This relationship can be expressed as $P=k(C^w/d^2)$, wherein P equals the peel force, $C^w$ equals the adhesive line coating weight, d equals the median diameter of the capsules and k equals a co-efficient relating to binder and substrate properties. The peel force should be in the range of 1.5 to 12 ounces per lineal inch, preferably 1.5 to 8.0 ounces per lineal inch. The coating weight of adhesive and microcapsules should be at a coating weight of approximately one pound for 300 to 800 square feet. Preferably the coating weight should be between approximately one pound for each 400 to 650 square feet. At higher coating weights, the surface of the cover sheets tend to tear, while at lower coating weights, the sheets tend to pull apart and the adhesive to paper bond tends to rupture in advance of the capsules included therein. The capsules should form between 20 and 90 percent by volume of the total adhesive composition, and preferably between 50 and 85 percent of the total composition volume. If certain microcapsule shell materials are used, such as gelatin, the capsule may comprise as much 100% of the adhesive compositions.

There are numerous advantages to the practice of the present invention and techniques for improving products using the present invention. The cost of the label inserts of the present invention is far less than the existing inserts which are equivalent to adding an additional page. The insertions of the label inserts of the present invention can be done with existing label application equipment. The label inserts can be preprinted before application. Perforated lines can be cut into the exposed surface so that multiple uses of the pull apart sheet are available, with each strip being pulled off separately. The artwork on the applied label may be the same as or different from the artwork over which it is applied. For example, the artwork over the label may show an unopened flower bud and the artwork under the label which is exposed upon removal of the top sheet and release of the fragrance may show an opened flower, thus providing a visual change as well as a change in scents. Similarly, the label could show the top of a perfume bottle with the stopper in it while the artwork underneath could show an open bottle. The residual, unbroken capsules could still be broken by scratching the surface, providing continued utility for the page after removal of the top sheet. Using labels, according to the present invention, it is also much simpler to apply multiple fragrances to a single page by applying more than one label with each label having a different fragrance.

The present invention enables the manufacture of a device for exposing a liquid (e.g., to the atmosphere), said device comprising:
(1) at least two sheets bound by an adhesive composition layer,
(2) said adhesive composition layer containing microcapsules with said liquid within the shell of said microcapsules, and
(3) said microcapsules having an average diameter between 4 and 80 micrometers,
the cohesive strength of the adhesive composition layer being less than the strength of the bond between said adhesive composition and a face of said sheets, the tensile rupture strength of said microcapsules being less than the cohesive strength of the adhesive composition, and the rupture force of said adhesive composition layer containing microcapsules at 50% relative humidity being between at least 1 ounce per linear five-and-one-half inches and less than 45 ounces per linear five-and-one-half inches (greater than 2.0 g/cm and less than 90 g/cm), at least one exterior surface of a sheet having a pressure-sensitive adhesive thereon. It is preferred that the rupture strength between the sheets excedes 8.0 g/cm and is less than 80 g/cm and most preferably excedes 16 g/cm and is less than 75 g/cm. The minimum strength at this ambient condition (i.e., 20° C. and 50% R.H.) is necessary to keep the sheets from falling apart from forces incurred during handling. This problem has frequently occurred in magazine inserts where coated paper was used. The maximum limit on the rupture strength is necessary to keep the paper from tearing (termed fiber pull or fiber rupture) before the adhesive an capsules rupture. This would prevent release of the liquid from the capsules. The adhesive strength of the pressure sensitive adhesive to substrates (especially printed coated paper) is preferably greater than the cohesive strength of the adhesive layer containing microcapsules. Preferably, it is at least 10% greater in adherence than the rupture strength between the sheets. A "liquid" according to the present invention includes liquids with materials dissolved or dispersed therein (e.g., pigments) and gels which are capable of flowing under moderate pressure.

It is also desirable to have the construction resist the effects of variable ambient conditions. It is therefore desirable that rupture strength excede 4.0 g/cm after storage at 120° C. and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 2 and 90 g/cm at 20° C. and 50% R.H.

A number of methods have been found which enable these conditions to be met according to the present invention. The use of viscosity increasing agents in the binder provides a more even coating and one that ruptures before fiber pull begins. The use of additional coatings over the coated paper which contain polymers different from the binder of the adhesive layer and which do not form a solution or chemically bond to the binder of the adhesive layer provides a useful article according to the present invention. The use of larger size capsules tends to weaken the cohesive strength of the adhesive composite and prevent fiber pull. The use of capsules which are not moisture sensitive in combination with these large capsules (i.e., greater than 30 microns and up to 95 microns) provides a useful adhesive layer. Higher capsule-to-binder ratios reduce the cohesive strength of the adhesive, as does the addition of non-viscosity enhancing particulate fillers.

According to the preferred practice of the present invention, if the method uses coated paper surfaces, the binder between the sheets contains viscosity increasers (viscofiers) in addition to the microcapsules. The use of viscofiers reduced the criticality of proportions of materials and provided increased coating and manufacturing latitude. viscosity enhancers or viscosity increasing agents are well known in the art. Any material which when present in the coating solution in an amount not greater than 10% by weight increases the viscosity by at least 5% is a viscofier according to the present invention. Preferably viscosity is increased by at least 20%. They are either inorganic particulate materials (e.g., silica, amorphous silica, bentonite clay, montmorillonite clay, etc.) or organic particulate or soluble materials (e.g., water softenable acrylic particles, water swellable poly(methylmethacrylate), water soluble or organic solvent soluble polymers, etc.). The inorganic particles tend to be preferred. The viscofiers enhancers have been found to be necessary in dry weight proportions of the adhesive mix in amounts of from 0.25 to 12% by weight, preferably from 5 to 12% by weight. In general, the weight proportions of materials in the dried adhesive layers according to the present invention are generally as follows:

| | |
|---|---|
| Microcapsules | 21–80% |
| Adhesive | 19.75–70% |
| Viscosity Enhancers | 0.25–12% |

Other optional ingredients such as surfactants, coating aids and the like may be present. Preferred proportions of these ingredients are:

| | |
|---|---|
| Microcapsules | 44.5–80% |
| Adhesive | 19.5–55% |
| Viscosity Enhancers | 0.5–10% |

The ability to use coated paper in the manufacture of these articles is important because those materials are the standard printing medium of the trade. Both one-side coated paper and two-side coated paper are useful. Those papers enable the highest quality printings to be made in combination with the releasable materials of the present invention.

The nature and composition of the adhesive binder is not critical to the practice of the invention as long as the required adhesive and cohesive properties are met. The adhesive may be pressure sensitive, water or solvent soluble or thermally activatable. A single layer of a non-pressure-sensitive adhesive is preferred. There is no need for rejoining the sheets after rupturing of the capsules and so the pressure sensitive function is not necessary.

The adhesive (with microcapsules) may be applied between two separate sheets in either a continuous or discontinuous patterns. It is usually desirable to leave at least some portion of at least one outer edge of the sheets unbonded so as to provide an area where separation can be easily started. A single sheet may be folded so as to form two facing sheets joined along one edge. The adhesive may be applied on the interior area adjacent the fold. This provides a folded article that can be readily opened, rupturing the capsules, yet leaves a single artifact rather than two sheets after use.

It is preferred that the capsule-bearing adhesive coated inside portion between the sheets constitute from 60 to 95% of the surface area of the sheets. In two sheet constructions, 10 to 95 percent adhesive coverage can be used to leave an edge or corner that can be readily grasped to pull one sheet form another. Some uses may allow for only a single corner to be uncoated so as to provide a starting point for the separation of the sheets, but the 60 to 95% range is preferred with 70 to 90% more preferred in two sheet constructions.

The pressure-sensitive adhesive usually covers 100% of the back side of the bottom sheet. This is desirable, but not essential. Stripes or other formats of discontinuous pressure-sensitive adhesive could be used.

Any class of adhesives including but not limited to polyurethanes, polyacrylates, polyvinyl resins (e.g., polyvinyl alcohol, polyvinyl chloride), polyamides, polyesters, polyolefins, starches, gum arabic, gelatin and the like may be readily used in the practice of the present invention. Washing of the capsules before mixing them with the adhesive often tends to provide more consistency in their properties by removing low molecular weight, unreacted materials.

In effect, to best practice the present invention it is desirable that certain properties within the article have relative values for each of the materials used. The cohesive strength of the sheet material should exceed the adhesive strength between the binder and the sheet. The adhesive strength of the binder to the sheet should exceed the cohesive strength of the binder and capsules therein. The cohesive strength of the binder should exceed the tensile rupture limits of the capsules. As previously noted, the size of the capsules has an important effect upon the practice of the present invention. With capsules less than 8 microns, there tends to be less rupturing of the capsules as to prevent the useful and efficient release of materials. Above 30 microns, the particles are so large that they are more readily burst by handling of the sheets and manufacturing procedures. Furthermore, with the large size particles it is extremely difficult to control bursting upon separation of the sheets because of increased effects upon adhesive and cohesive properties of materials in contact with the capsules. The preferred ranges of 8 to 30 and 15 to 25 microns is important to the practice of the present invention. Within these limits, rupture in excess of 50 percent of the capsules can be easily obtained. Rupture in excess of 80 percent of the capsules can often be accomplished in the practice of the present invention within those limits.

The capsules may contain a wide variety of active materials therein. The least useful of materials to be included therein would be coloring agents since separation of the sheets would generally produce uniform coloration rather than a distinct image. The most preferred types of ingredients would be fragrant materials (such as essences and perfumes) or materials which provide chemically active vapors or liquids (e.g., bacteriostats or deodorants) to be wiped on or transferred to another surface. These may or may not also be colored. For example, a testing kit for the presence of chemical vapors could be produced by providing material within the capsules which would react in the vapor phase with the material for which a leak is being investigated. By separating the sheet, rupturing the capsules and exposing the vapor test material, a color forming reaction in the air or on the sheet could be readily observable. Another particularly useful format would be to include the microcapsules within a water-remoistenable adhesive and to use the mixture as the binding adhesive for novelty envelopes. For example, the microcapsules could contain the aromatic essence of baby oil, cake or pizza for invitation envelopes for a baby shower, wedding (or birthday party), or general party, respectively. The sides of the sheets with the capsule-bearing adhesive thereon are preferably printed under the adhesive or adjacent to the adhesive.

This invention may be practiced with a number of various modifications that provide new and useful articles and processes. For example, the adhesive composition with capsules may be associated with various printed formats to form novelty items. The exterior sheets or exposed inner face of the sheets may have questions or stories or rhymes, and under the adhesive may be a printed picture answering the question, depicting the story or completing the rhyme, with the released fragrance emphasizing the picture further.

These and other aspects of the present invention will be shown in the following examples.

EXAMPLE 1

A 70 lb stock of one side coated paper was used as the top sheet 2 of the label 14. A slurry was prepared from rose fragrance in urea-aldehyde microcapsules manufactured according to the process of Example 10 of U.S. Pat. No. 3,516,941. The slurry contained 64% dry weight of capsules, 24.50% dry weight of poly(vinyl alcohol) (Gelvatol ® 40-10), 10.50% poly(vinyl alcohol) (Gelvatol ® 20-60), and 1% glycerin in water. The slurry was applied to 85% of the surface of the uncoated face of a continuouos web of pressure sensitive label stock at a coating weight of 3.5 pounds per 1300 ft$^2$. After the slurry was applied, the uncoated face of the top sheet was mated to the slurry coated face of the label stock. The laminate was then die-cut into appropriate sizes (e.g., 3×8 cm). The cut labels were then removed and affixed to a printed page. The edge of the top sheet which was over the uncoated surface of the label stock was easily raised and grasped by one hand. Upon pulling the top sheet, fragrance was released and the bottom sheet remained firmly adhered to the printed page.

Mechanical handling of the labels by a label applicator did not produce any intolerable level of capsule breakage.

When perforated lines were die-cut into the surface of the top layer, individual strips could be pulled off, leaving the bottom layer adhered to the printed page and leaving additional strips to be pulled off.

We claim:
1. A label for application to a surface, said label comprising
   (1) at least two sheets, a top sheet and a bottom sheet, bound by an adhesive composition layer,
   (2) said adhesive composition layer containing microcapsules with a liquid within the shell of the microcapsules,
   (3) said microcapsules having an average diameter between 4 and 80 micrometers, and
   (4) said bottom sheet having a pressure-sensitive adhesive on an exterior surface
the cohesive strength of the adhesive composition layer being less than the strength of the bond between said adhesive composition and the faces of said sheets, the tensile rupture strength of said microcapsules being such that the cohesive failure of the adhesive results in breakage of the microcapsules, and the tensile rupture strength between said two sheets being at least 1.0g/cm and less than 90 g/cm at 20° C. and 50% relative humidity.

2. The device of claim 1 wherein said adhesive composition comprises said microcapsules, a polymeric binder and a viscosity increaser.

3. The device of claim 2 wherein said surfaces are on flexible sheets of coated paper and said viscosity increaser comprise from 0.25 to 25% by dry weight of said adhesive composition layer.

4. The device of claim 1 wherein said sheets are coated paper coated on both faces with a resinous binder and pigment.

5. The device of claim 1 wherein said microcapsules have an average diameter between 8 and 30 micrometers.

6. The device of claim 1 wherein said pressure-sensitive adhesive has a strippable cover sheet attached thereto.

7. The device of claim 4 wherein said pressure-sensitive adhesive has a strippable cover sheet attached thereto.

8. The device of claim 2 wherein said microcapsules comprise gelatin and are between 21 and 100% by weight of said adhesive composition, said binder comprises between 0 and 78.75% by weight and said viscosity increaser comprises between 0.25 and 12% by weight.

9. The device of claim 4 wherein said microcapsules comprise between 50 and 85% by volume of said adhesive composition and are formed of a urea-aldehyde polymer.

10. The device of claim 5 wherein said microcapsules comprise between 50 and 85% by volume of adhesive composition and comprise a polymeric shell material.

11. The device of claim 1 wherein said top sheet has perforated lines thereon to enable removal of individual portions of said top sheet.

12. The device of claim 1 wherein said liquid is an odor releasing material and the shell of said microcapsule comprises a urea-formaldehyde resin.

13. The device of claim 2 wherein said liquid is an odor releasing material and said adhesive on an exterior surface is a thermal adhesive.

14. The device of claim 3 wherein said liquid is an odor releasing material and said adhesive on an exterior surface is a thermal adhesive.

15. The device of claim 1 wherein the image that appears on the outer surface of the top sheet is the same as the image that appears on the interior surface of the bottom sheet.

16. The device of claim 6 wherein said liquid is an odor releasing material and said adhesive on an exterior surface is a thermal adhesive.

17. The device of claim 8 wherein said liquid is an odor releasing material and said adhesive on an exterior surface is a thermal adhesive.

18. The device of claim 1 wherein the image that appears on the outer surface of the top sheet is different from the image that appears on the interior surface of the bottom sheet.

19. The device of claim 4 wherein the image that appears on the outer surface of the top sheet is different from the image that appears on the interior surface of the bottom sheet.

20. The device of claim 6 wherein the image that appears on the outer surface of the top sheet is different from the image that appears on the interior surface of the bottom sheet.

* * * * *